(12) United States Patent
Schwarz et al.

(10) Patent No.: US 11,092,544 B2
(45) Date of Patent: Aug. 17, 2021

(54) METHOD AND DEVICE FOR DETERMINING A FINISHED MEDICINAL PRODUCT

(71) Applicant: Medios Manufaktur GmbH, Berlin (DE)

(72) Inventors: Jörg Schwarz, Wilster (DE); David Mainka, Berlin (DE)

(73) Assignee: Ayna Analytics GmbH, Kleinmachnow (DE)

( * ) Notice: Subject to any disclaimer, the term of this patent is extended or adjusted under 35 U.S.C. 154(b) by 0 days.

(21) Appl. No.: 16/772,528

(22) PCT Filed: Dec. 13, 2018

(86) PCT No.: PCT/EP2018/084818
§ 371 (c)(1),
(2) Date: Jun. 12, 2020

(87) PCT Pub. No.: WO2019/115720
PCT Pub. Date: Jun. 20, 2019

(65) Prior Publication Data
US 2020/0386679 A1    Dec. 10, 2020

(30) Foreign Application Priority Data

Dec. 14, 2017  (EP) .................................... 17207496

(51) Int. Cl.
*G01J 3/00*    (2006.01)
*G01N 21/359*    (2014.01)
*G01N 33/15*    (2006.01)

(52) U.S. Cl.
CPC ........... *G01N 21/359* (2013.01); *G01N 33/15* (2013.01); *G01N 2201/0636* (2013.01)

(58) Field of Classification Search
CPC .. G01N 21/314; G01N 21/33; G01N 21/3504; G01J 3/10; G01J 3/42
USPC ......................................................... 356/51
See application file for complete search history.

(56) References Cited

U.S. PATENT DOCUMENTS

2007/0008523 A1  1/2007  Kaye et al.
2009/0262351 A1  10/2009  Erickson et al.

FOREIGN PATENT DOCUMENTS

DE    10326152    1/2005
DE    102010013335  3/2011

*Primary Examiner* — Md M Rahman
(74) *Attorney, Agent, or Firm* — Boyle Fredrickson S.C.

(57) ABSTRACT

The invention relates to a method for determining a finished medicinal product, having the following steps: providing a finished medicinal product to be determined in closed primary packaging; measuring an NIR measurement spectrum for the finished medicinal product to be determined through the closed primary packaging; comparing the NIR measurement spectrum with an NIR reference spectrum, which is associated with a medicinal product or an active ingredient of a medicinal product; and determining that the finished medicinal product to be determined contains the medicinal product or the medicinal product active ingredient when the NIR measurement spectrum and the NIR reference spectrum correspond within a margin for error. The invention further relates to a device for determining a finished medicinal product.

12 Claims, 7 Drawing Sheets

METHOD AND DEVICE FOR DETERMINING A FINISHED MEDICINAL PRODUCT

BACKGROUND

Finished medicinal products can be inspected after their production, for example to verify the correct composition of the medicinal product. It is also possible to provide for metrological testing to detect adulterations or impure imitation products. To perform such a determination of the finished medicinal product, said product is arranged in a sample container to perform the determination. If the finished medicinal product is already packaged, it is removed from the primary packaging and then arranged in the sample container in which the sample is tested.

SUMMARY

The object of the invention is to provide a method and a device for determining a finished medicinal product with which the finished medicinal product can be determined in an efficient and material-protecting manner.

To achieve the object, a method as well as a device for determining the finished medicinal product are devised in accordance with the independent claims 1 and 13. Embodiments are described in the dependent subclaims.

According to one aspect, a method for determining a finished medicinal product is provided that has the following steps: providing a finished medicinal product to be determined in closed primary packaging; measuring an NIR measurement spectrum for the finished medicinal product to be determined through the closed primary packaging; comparing the NIR measurement spectrum with an NIR reference spectrum, which is associated with a medicinal product or an active ingredient of the medicinal product; and determining that the finished medicinal product to be determined contains the medicinal product or the medicinal product active ingredient if the NIR measurement spectrum and the NIR reference spectrum correspond within a margin for error.

According to a further aspect, a device for determining a finished medicinal product is provided. The device comprises a test sample receptacle, which is adapted to receive as a test sample a finished medicinal product to be determined through a closed primary packaging. A measuring device is provided, which is adapted to record an NIR measurement spectrum for the finished medicinal product to be determined through the closed primary packaging. The device furthermore comprises an evaluation unit, which is adapted to compare the NIR measurement spectrum with an NIR reference spectrum, which is associated with a medicinal product or a medicinal product active ingredient, and to determine that the finished medicinal product to be determined contains the medicinal product or the medicinal product active ingredient if the NIR measurement spectrum and the NIR reference spectrum correspond within a margin for error.

Using the technology proposed, it is possible to optically determine or to metrologically test the finished medicinal product without having to remove it from the primary packaging. The closed primary packaging therefore is not damaged. Since the measurement is performed through the closed primary packaging, the measuring process is simplified since, for example, even any accidental contact with the finished medicinal product is avoided. Furthermore, any microbiological contamination is avoided.

It may be provided that a plurality of measurements are performed for the finished medicinal product and that the respectively measured NIR spectrums are averaged before the comparison with the NIR reference spectrum/spectrums is carried out. The NIR reference spectrum may also be the result of a plurality of measurements, the result of which is averaged.

If the NIR spectrums that are compared do not correspond, this means that the spectrums within the margin for error do not correspond and thus differ in view of the margin for error.

To prepare for the comparison of the NIR measurement spectrum with the NIR reference spectrum, it may be provided that the spectrums are processed or prepared. The spectrum preparation methods include, for example, vector normalization. As part of this process, for example, the average values for the measured optical parameter (absorption, transmission, reflection) are determined first in order to then deduct the average values from the measurement spectrum. This data preparation may be performed for all or some of the spectral values (wavelength, wave number). Alternatively or additionally, it is possible to provide as part of the processing of the measurement spectrums that a first, a second and/or a third derivative is determined for the measured values. It is also possible to use other normalization methods, either alternatively or additionally.

Following such a data preprocessing, which may comprise one or more of the aforementioned steps, an evaluation by means of chemometric methods may be provided. The NIR measurement spectrum and the NIR reference spectrum, which may both be processed in accordance with a respectively selected data preprocessing, are compared. The spectral distance, for example, may be determined for the spectral comparison. If the result is a spectral distance that does not exceed a threshold, the spectrums are determined as equal or similar. Various methods as are known for the determination of the spectral distance. These include, for example, the Euclidean distance and the Mahalanobis distance.

The comparison of the NIR measurement spectrum with the NIR reference spectrum may furthermore include or comprise the following: determining of a first spectral subrange from a total spectral range detected during the measurement of the NIR measurement spectrum, comparing the NIR measurement spectrum and the NIR reference spectrum for the first spectral subrange, and determining that the finished medicinal product to be determined contains the medicinal product or the medicinal product active ingredient if the NIR measurement spectrum and the NIR reference spectrum correspond in the first spectral subrange within a first margin for error. In this embodiment, the comparison between the NIR measurement spectrum and the NIR reference spectrum is performed at least for the first spectral subrange, which represents a section of the overall spectral range for which the NIR measurement spectrum was taken. In an alternative embodiment, it may be provided that the first spectral subrange corresponds to the overall spectral range if, for example, the measurement of the NIR spectrum is limited from the beginning to the first spectral subrange, which was selected for the measurement of the medicinal product to be determined.

The comparison of the NIR measurement spectrum with the NIR reference spectrum may furthermore comprise the following: determining a second spectral subrange from an overall spectral range captured during the measurement of the NIR measurement spectrum, wherein the second spectral subrange is separated from the first spectral range within the overall spectral range; comparing the NIR measurement spectrum and the NIR reference spectrum for the second spectral subrange; and determining that the finished medicinal product to be determined contains the medicinal product or the medicinal product active ingredient if the NIR measurement spectrum and the NIR reference spectrum in the second spectral subrange correspond within a second margin for error. In this embodiment, a comparison of the NIR measurement spectrum and the NIR reference spectrum in at least a second spectral subrange is provided in addition to the spectral analysis performed by means of a comparison in the first spectral range. The second spectral subrange is different from the first spectral subrange and may optionally, however, overlap therewith in some portions. It may thus be provided that the second spectral subrange completely overlaps with the first spectral range, for example, such that the second spectral subrange captures a subrange within the first spectral subrange.

The second margin for error may differ from the first margin for error. Alternatively, the two margins of error may be the same. In this or other embodiments, a threshold may be used, for example, for the spectral distance, for example the Euclidian distance or Mahalanobis distance. A plurality of thresholds may be applied in the different embodiments as well so that it is determined that the finished medicinal product to be determined contains the medicinal product or the medicinal product active ingredient if the NIR measurement spectrum and the NIR reference spectrum each correspond within the plurality of margins for error. If a plurality of margins for error are used for the comparison, in particular relating the different spectral comparison methods, it may be specified that the fulfillment of the margin for error condition for only a portion of the tested margins for error suffices to determine that the finished medicinal product to be determined contains the medicinal product or the medicinal product active ingredient.

The NIR measurement spectrum may be compared with a plurality of NIR reference spectrums from a spectral reference library. A plurality of NIR reference spectrums may be provided in the spectral reference library, in particular in a classified arrangement. A subsection of the library may relate to a classification of various medicinal product active ingredients for which one or a plurality of NIR reference spectrums are provided in each case, which differentiate the associated medicinal product active ingredient from other medicinal product active ingredients. Similarly, a library for different finished medicinal products may be provided. To assess the correspondence within the margin for error, spectral ranges (wavelength ranges), for example, may be defined as classification criteria that are analyzed for a specific finished medicinal product or a specific medicinal product active ingredient during the comparison of the NIR measurement spectrum with the NIR reference spectrum.

The finished medicinal product to be determined may be in a closed disposable primary packaging. With respect to disposable or reusable primary packaging, it may be provided that the respective packaging is closed with a single-use closure.

The finished medicinal product to be determined may be arranged in sterile packaging.

The finished medicinal product to be determined may be in a container of the closed disposable primary packaging, which container is made of glass and/or plastics material. The container for the finished medicinal product may have various shapes, for example a round glass container or a blister pack. In the case of a round container made of glass or plastics material, it may be provided that the NIR beams are irradiated through the bottom of the container during the measurement.

During the measuring of the NIR measurement spectrum, at least one optical measuring method from the following group of measuring methods may be used: absorption measurement, reflection measurement and transmission measurement. During the comparison of the NIR measurement spectrum and the NIR reference spectrum, spectrums for one or more of the optical measuring methods may be included.

The NIR measurement spectrum may be compared with an NIR reference spectrum which is associated with a medicinal product active ingredient formed as a biosimilar. Biosimilars are biotechnologically manufactured medicinal products. They may be secondary products of biopharmaceuticals. Their active ingredient is comparable with the active ingredient of the already approved, biotechnologically manufactured medicinal product ("reference product"). Frequently, biosimilars are large, complex molecules.

The finished medicinal product to be determined may be determined as containing the medicinal product active ingredient trastuzumab emtansine if the NIR measurement spectrum and the NIR reference spectrum correspond in a first spectral subrange from 3500 $cm^{-1}$ to 5500 $cm^{-1}$, alternatively from 4000 $cm^{-1}$ to 5000 $cm^{-1}$, and further alternatively from 4150 $cm^{-1}$ to $5150^{-1}$ within the first margin for error.

The finished medicinal product to be determined may be determined as containing the medicinal product active ingredient infliximab (originator) if the NIR measurement spectrum and the NIR reference spectrum correspond in a first spectral subrange from 3500 $cm^{-1}$ to 5500 $cm^{-1}$, alternatively from 4000 $cm^{-1}$ to 5000 $cm^{-1}$, and further alternatively from 4550 $cm^{-1}$ to $4750^{-1}$ within the second margin for error.

The finished medicinal product to be determined may be determined as containing the medicinal product active ingredient nab-paclitaxel if the NIR measurement spectrum and the NIR reference spectrum correspond in a first spectral subrange from 5600 $cm^{-1}$ to 7000 $cm^{-1}$ and in a second spectral subrange from 4000 $cm^{-1}$ to 5000 $cm^{-1}$ within the first margin for error.

The determination of whether the finished medicinal product to be determined contains the medicinal product or the medicinal product active ingredient within the meaning used here relates to the identification of the medicinal product and/or the medicinal product active ingredient and/or the identification and the differentiation of deviations between like medicinal products and/or between like medicinal product active ingredients. The technology described may be used to identify the medicinal product and/or the medicinal product active ingredient or to identify and differentiate between like medicinal products and/or between like medicinal product active ingredients.

The embodiments explained above may be provided accordingly in conjunction with the device for determining a finished medicinal product.

DESCRIPTION OF EMBODIMENTS

Further embodiments are explained in more detail below with reference to the drawings. In the drawings:

FIG. 1 is a schematic representation of a device for determining a finished medicinal product by means of NIR spectroscopy. The NIR spectral range captures wavelengths in the range from 780 nm to 2,500 nm (12,800 to 4,000 cm$^{-1}$ wave number).

Figure 1:
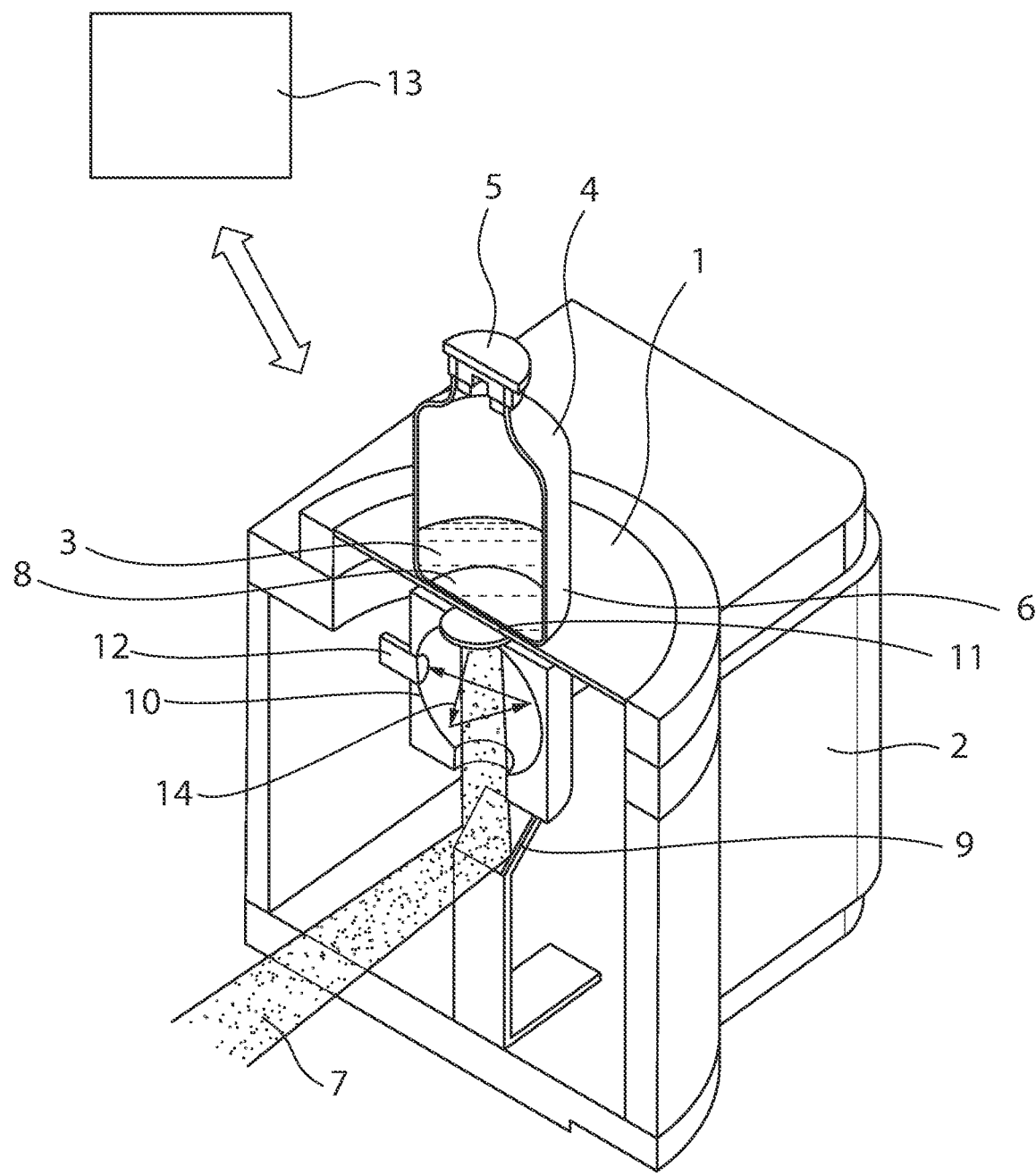
FIG. 1 is a schematic representation of a device for determining a finished medicinal product using NIR spectroscopy.

A sample 3 of a finished medicinal product to be determined in primary packaging 4 is arranged on a sample receptacle 1 of a measuring device 2. A closure 5 of the primary packaging 4 is a single-use closure. The primary packaging 4 is formed with a container 6, which is made, for example, of plastics material or glass, such as brown glass.

The sample 3 of the finished medicinal product to be determined is inspected in the closed primary packaging 4 by irradiating NIR light beams 7 across the region of the bottom 8 of the container 6, which beams penetrate the container wall and thus arrive at the sample 3. Prior to this process, the NIR light beams 7 are preferably deflected by a mirror 9 and guided through an Ulbricht sphere 10. For a measurement, a further mirror 11 is displaced from the position shown in FIG. 1 so that the beam path on the bottom 8 of the container 6 is released.

Due to the irradiation of the NIR light beams 7 on the sample 3, NIR measurement light beams (not shown) are created, which travel from the container 6 to the Ulbricht sphere 10 and are deflected there toward a detector 12, along a path 14.

With the further mirror 11, the beam path can be interrupted and opened. The interruption shown in FIG. 1 may, for example, be used for a reference measurement, i.e., for a measurement without a sample effect, for example so as to improve the signal-to-noise ratio. When the further mirror 11, which is configured as a gold mirror, for example, is arranged in the beam path, the irradiated NIR light beams 7 according to FIG. 1 are refracted without reaching the sample 3 and arrive at the detector 12. If the further mirror 11 is arranged laterally to the beam path (not shown), the measurement can be carried out on the sample 3 which is to be determined.

Furthermore, an evaluation unit 13 is provided in which the NIR measurement spectrums captured by means of the detector 12 can be processed and compared with the NIR reference spectrums. The evaluation unit may comprise one or more processors and a memory in which a software application is stored with which the processing of the spectral signals measured can be executed.

Figure 2:
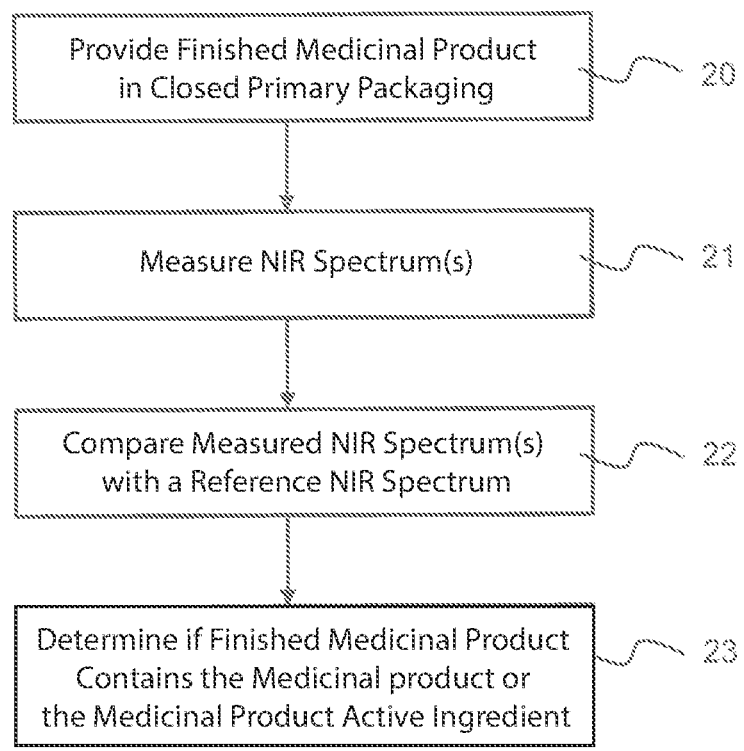
FIG. 2 is a schematic representation of a method for determining a finished medicinal product.
Figure 3:
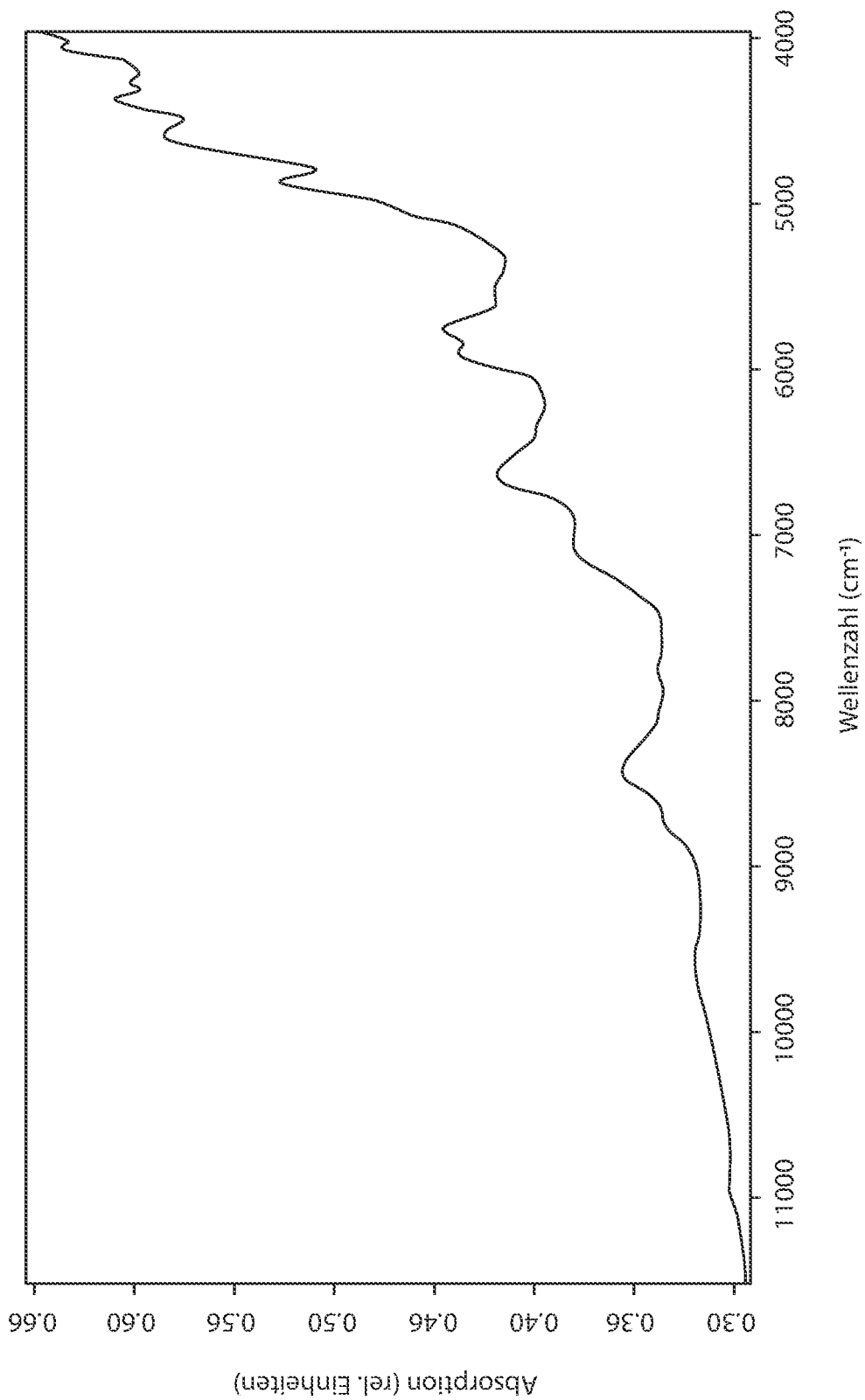
FIG. 3 is a graphic representation of an NIR measurement spectrum for Abraxane (nab-paclitaxel), wherein the absorption and dependence on the wave number is shown.
Figure 4:
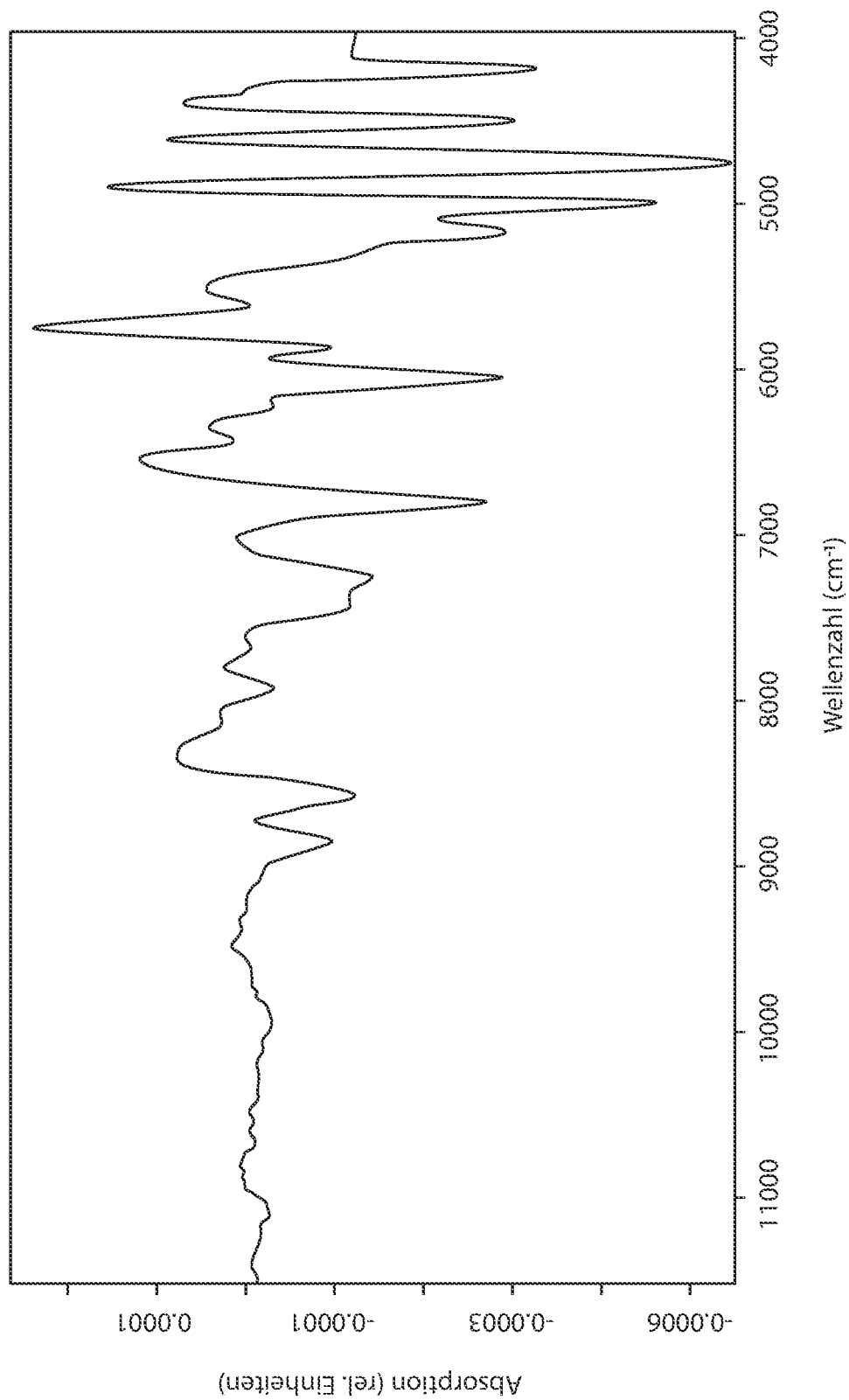
FIG. 4 is a graphic representation of the first derivative for the NIR measurement spectrum from FIG. 3.
Figure 5:
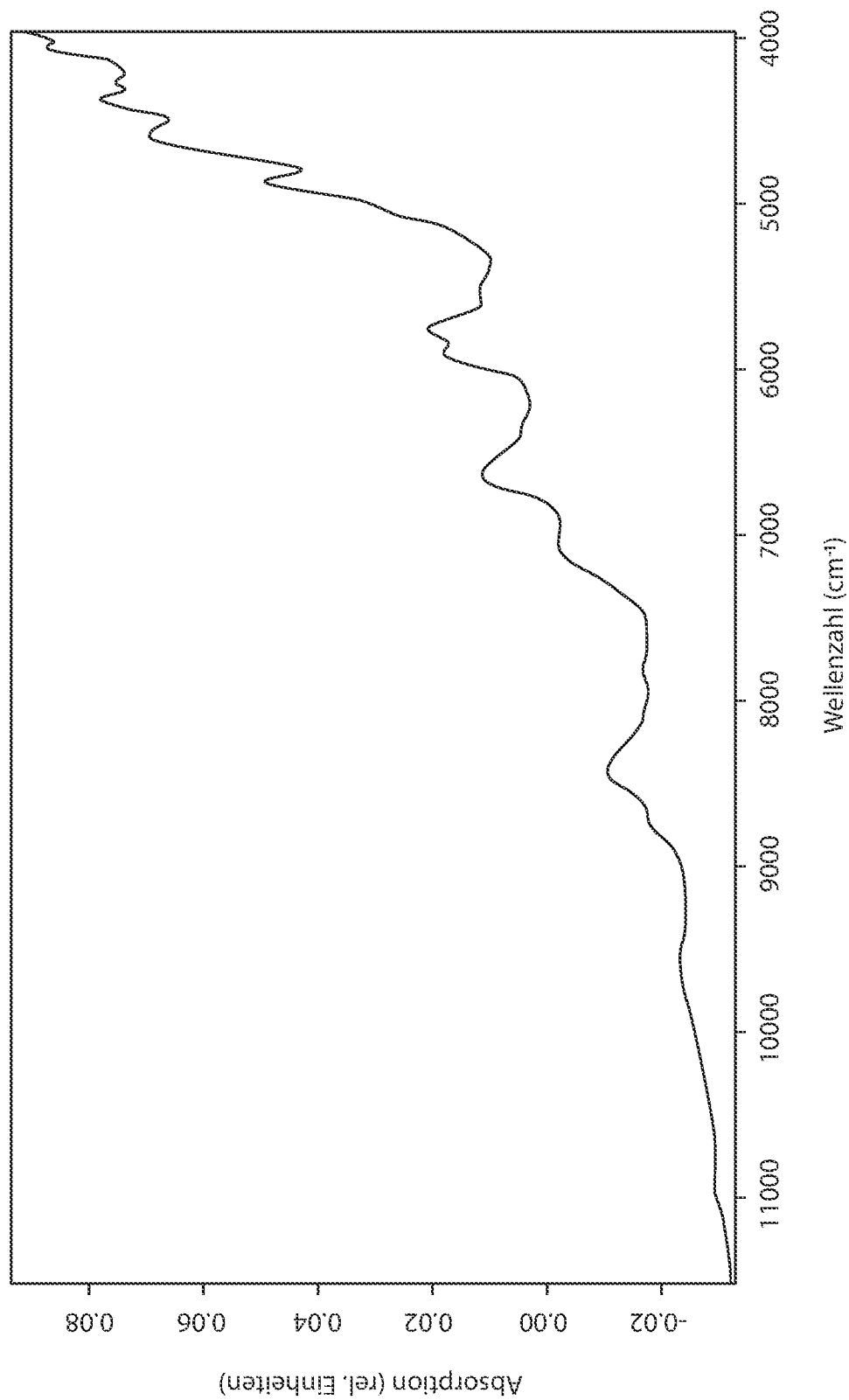
FIG. 5 is a graphic representation of the vector-normalized NIR measurement spectrum from FIG. 3.

FIG. 2 is a schematic representation of the course of a method for determining a finished medicinal product. In step 20, the finished medicinal product to be determined is provided in the closed primary packaging 3. In step 21, one or a plurality of NIR measurement spectrums are measured, wherein the NIR light beams 6 are irradiated through the closed primary packaging 3. The NIR measurement spectrum is compared with an NIR reference spectrum (step 22), which is associated with a medicinal product or a medicinal product active ingredient. By means of the evaluation unit 12, it is determined whether the finished medicinal product to be determined contains the medicinal product or the medicinal product active ingredient (step 23) if the NIR measurement spectrum and the NIR reference spectrum correspond within a margin for error.

Chemometric methods are used for evaluating and comparing NIR measurement spectrums and NIR reference spectrums. For example, these may include a data preprocessing, whereupon the chemometric evaluation takes place. In the context of data preprocessing of the spectrums, a vector normalization may be performed, for example. One or more derivatives for the spectrums may be calculated as well. The generally known Savitzky-Golay algorithm may be used to derive the spectrums.

In the context of the chemometric evaluation, the spectrums (which may have been pretreated) are then compared. In particular, a spectral distance between the spectrums to be compared is determined. Various methods for the calculation of the spectral distance are known. The Euclidian distance may be determined, for example. Alternatively or additionally, it may be provided that the Mahalanobis distance is determined to identify the similarity of the spectrums to be compared within the specified margin for error.

Further embodiments are explained below. The NIR measurements were determined at room temperature.

Figure 6:
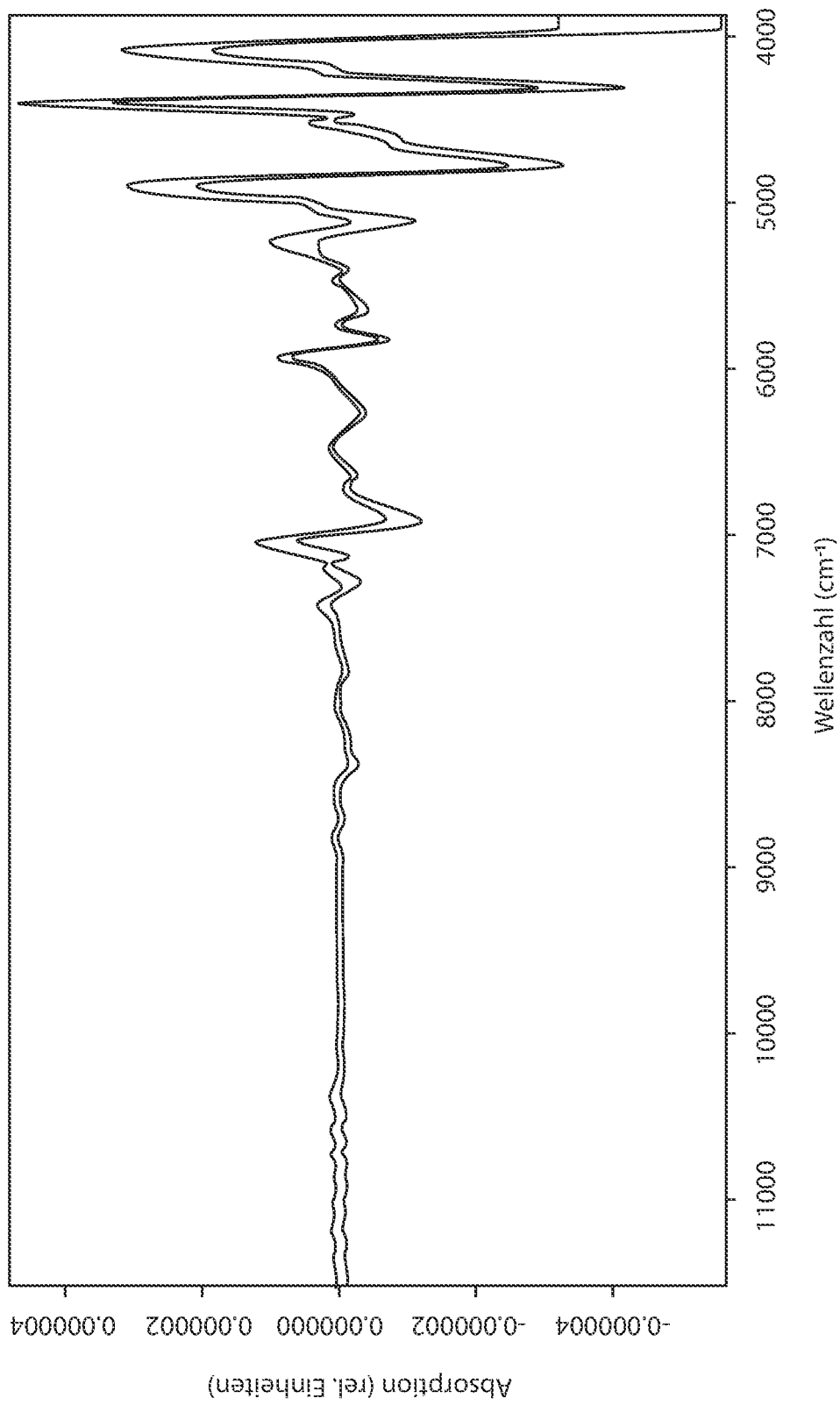
FIG. 6 is a graphic representation of preprocessed NIR spectrums for four finished medicinal products.

The finished medicinal product Remicade contains the medicinal product active ingredient infliximab. This medicinal product constitutes the original product. At least one biosimilar, sold by various companies, is known. By means of a wavelength range selection from approximately 4592 cm$^{-1}$ to approximately 4736 cm$^{-1}$, the originator can be distinguished from the biosimilar (cf. pretreated, complete spectrums of four finished medicinal products in FIG. 6). The embodiments concern Remicade and the related biosimilars: Remisa, Inflectra and Flixabi.

Figure 7:
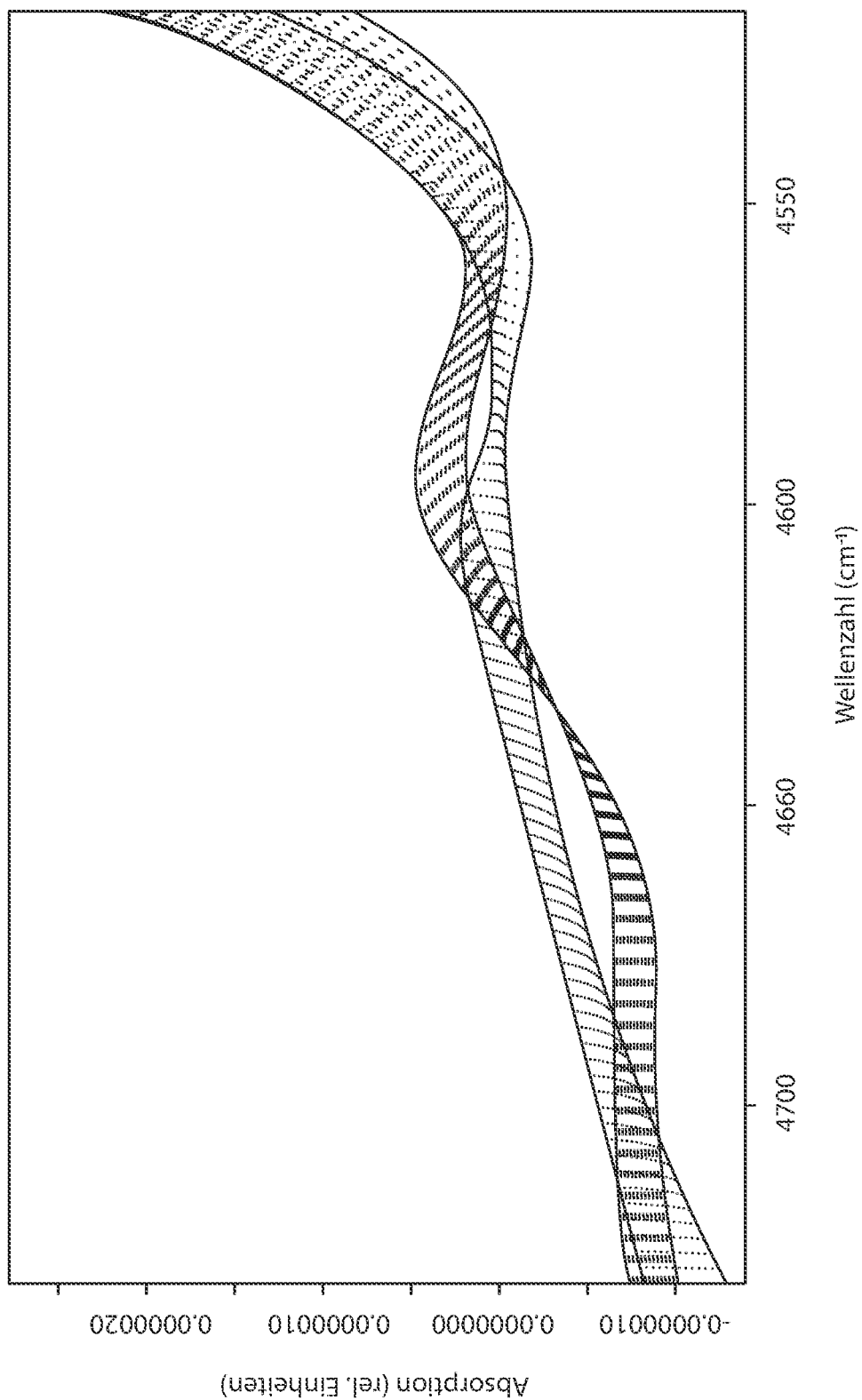
FIG. 7 is a graphic representation of a spectral section for the NIR spectrums from FIG. 6.

The spectral differences shown in FIG. 7 lead to the fact that the two active ingredients (originator and biosimilar), which, based on tests, differ in their glycosylation pattern (cf., for example, "arznei-telegramm", 6/15, 46th volume, 12 Jun. 2015), can be distinguished. This is generally possible only with a complex LC-MS method.

The method for determining a finished medicinal product was used in one embodiment for determining Remicade in a finished medicinal product. For this purpose, a plurality of consecutive comparison steps were performed for the comparison of NIR measurement spectrums and NIR reference spectrums in which selected spectral ranges were compared to achieve the determination or identification of one or more active ingredients in the respective step or to exclude them.

Table 1 below shows a summary overview of the comparison steps that were performed.

TABLE 1

| Steps | Description | Wave number range(s) [cm$^{-1}$] |
|---|---|---|
| 1 | Dividing into groups | 10040-4080 |
| 2 | Determining Kyprolis and separating a further group of chemically defined medicinal product active ingredients | 7760-7200; 6992-5336; 5136-4104 |
| 3 | Determining Abraxane | 6904-5600; 5000-4000 |
| 4 | Determining Etopophos | 6968-6584 |
| 5 | Determining Orencia, Ivemend and separating from Adcetris and Myocet | 6856-5400, 4992-4776, 4400-4136 |
| 6 | Determining Entyvio | 6192-6128; 5592-5544; 5096-4952 |

TABLE 1-continued

| Steps | Description | Wave number range(s) [cm$^{-1}$] |
|---|---|---|
| 7 | Determining Yondelis, separating into two groups | 7016-5384; 5008-4072 |
| 8 | Dividing into two groups | 6000-5600; 4904-4144 |
| 9 | Determining Remicade and/or biosimilars | 4736-4592 |

In the spectral comparison steps, the NIR measurement spectrum is always compared with one or more NIR reference spectrums. In step 1, a rough separation into groups A and B is performed on the basis of the wave number range from approximately 10,040 cm$^{-1}$ to approximately 4,080 cm$^{-1}$. All the NIR spectrums are normalized in this step and the data is preprocessed to minimize physical factors that influence the spectrum. To prepare for the comparison, it is provided here that the spectrums are prepared. Vector normalization is one of the methods used to prepare the spectrums. In this method, average values are first determined for the measured optical parameter in order then to deduct the average values from the measurement spectrum, wherein this data preparation may be performed for all or some of the spectral values (wavelength, wave number). Alternatively or additionally, it may be provided that derivatives are determined for the measured values. Afterwards, the spectrums are compared. For this purpose, for example, the Euclidean distance and/or the Mahalanobis distance may be used.

In the next step 2, the separation of Kyprolis and a group of chemically defined cytostatic drugs is performed. In this process, the interfering water bands are excluded. In addition, a pretreatment similar to the one in step 1 is performed with the individually optimized settings. The separation is performed by means of the Mahalanobis distance.

In step 3, Abraxane is identified or determined, i.e., it is ruled out that it is Abraxane.

Analogously, Etopophos is identified in step 4, Adcentris, Myocet, Ivemend and Orencia in step 5 and Entyvio in step 6.

In step 7, Yondelis is identified or determined and a further division into two groups is performed. In step 8, a further distinction is made between two groups of monoclonal antibodies. One group now still only contains the different Infliximab FAM. These are differentiated in step 9 with the specific wave number range.

Table 2 below shows further embodiments for the determination of active ingredients in finished medicinal products by means of the technology described.

TABLE 2

| Cons. No. | Active ingredient in the medicinal product | Wave number range(s) [cm$^{-1}$] | Product example |
|---|---|---|---|
| 1 | Nab-paclitaxel | 7100-550, 5000-4000 | Abraxane 100 mg Celgene |
| 2 | Brentuximab vedotin | 5000-4000 | Adcetris 50 mg Takeda |
| 3 | Pemetrexed | 6300-5900, 5200-4900 | Alimta 500 mg Lilly |
| 4 | Belimumab | 5900-5300 | Benlysta 120 mg gsk |
| 5 | Belimumab | 5900-5300 | Benlysta 400 mg gsk |
| 6 | Vedolizumab | 6300-6000, 5600-4800 | Entyvio 300 mg Tadeka |
| 7 | Infliximab (biosimilar) | 4800-4300 | Flixabi 100 mg SamsungBioe-pis |
| 8 | Trastuzumab | 5900-5300 | Herceptin 150 mg Roche |
| 9 | Infliximab (biosimilar) | 4800-4300 | Inflectra 100 mg Hospira |
| 10 | Trastuzumab emtansine | 4900-4400 | Kadcyla 100 mg Roche |
| 11 | Trastuzumab emtansine | 4900-4400 | Kadcyla 160 mg Roche |
| 12 | Pembrolizumab | 4900-4400 | Keytruda 50 mg MSD |
| 13 | Doxorubicin | 5000-4000 | Myocet 50 mg TEVA |
| 14 | Abatacept | 7000-5300, 5100-4000 | Orencia 250 mg b-ms |
| 15 | Infliximab (original) | 4800-4300 | Remicade 100 mg MSD |
| 16 | Infliximab (biosimilar) | 4800-4300 | Remsima 100 mg Celltrion |
| 17 | Bortezomib | 7100-6400, 6200-5800, 5300-4900 | Velcade 3.5 mg Janssen |
| 18 | Azacitidin | 6300-5900, 5200-4900 | Vidaza 100 mg Celgene |

The features disclosed in the description above, the claims and the drawings may be of significance for the realization of the different embodiments both individually and in any combination.

The invention claimed is:

1. A method for determining a finished medicinal product having the following steps:
   providing a finished medicinal product to be determined in closed primary packaging;
   measuring an NIR (near infrared) measurement spectrum for the finished medicinal product to be determined through the closed primary packaging;
   comparing the NIR measurement spectrum with an NIR (near infrared) reference spectrum, which is associated with a medicinal product or an active ingredient of a medicinal product, wherein the NIR measurement spectrum is compared with the NIR reference spectrum which is assigned to a medicinal product active ingredient formed as a biosimilar; and
   determining that the finished medicinal product to be determined contains the medicinal product or the medicinal product active ingredient when the NIR measurement spectrum and the NIR reference spectrum correspond within a margin for error.

2. The method according to claim 1, characterized in that the comparison of the NIR measurement spectrum with the NIR reference spectrum furthermore has the following steps:
   determining a first spectral subrange of an overall spectral range captured during the measurement of the NIR measurement spectrum;
   comparing the NIR measurement spectrum and the NIR reference spectrum for the first spectral subrange; and
   determining that the finished medicinal product to be determined contains the medicinal product or the medicinal product active ingredient when the NIR measurement spectrum and the NIR reference spectrum in the first spectral subrange correspond within a first margin for error.

3. The method according to claim 2, characterized in that the comparison of the NIR measurement spectrum with the NIR reference spectrum furthermore has the following steps:
   determining a second spectral subrange of an overall spectral range captured during the measurement of the NIR measurement spectrum, wherein the second spectral subrange within the overall spectral range is separated from the first spectral range;
   comparing the NIR measurement spectrum and the NIR reference spectrum for the second spectral subrange; and determining that the finished medicinal product to be determined contains the medicinal product or the medicinal product active ingredient if the NIR measurement spectrum and the NIR reference spectrum in the second spectral subrange correspond within a second margin for error.

4. The method according to claim 3, characterized in that the second margin for error is different from the first margin for error.

5. The method according to claim 3, characterized in that the finished medicinal product to be determined is determined as containing the medicinal product active ingredient nab-paclitaxel when the NIR measurement spectrum and the NIR reference spectrum correspond in a first spectral subrange from 5600 cm$^{-1}$ to 7000 cm$^{-1}$ and in a second spectral subrange from 4000 cm$^{-1}$ to 5000 cm$^{-1}$ within a first margin for error.

6. The method according to claim 2, characterized in that the finished medicinal product to be determined is determined as containing the medicinal product active ingredient trastuzumab emtansine when the NIR measurement spectrum and the NIR reference spectrum correspond in a first spectral subrange from 3500 cm$^{-1}$ to 5500 cm$^{-1}$, alternatively from 4000 cm$^{-1}$ to 5000 cm$^{-1}$ and further alternatively from 4150 cm$^{-1}$ to 5150 cm$^{-1}$ within the first margin for error.

7. The method according to claim 2, characterized in that the medicinal product active ingredient is determined as containing infliximab (originator) if when the NIR measurement spectrum and the NIR reference spectrum correspond in a first spectral subrange from 3500 cm$^{-1}$ to 5500 cm$^{-1}$, alternatively from 4000 cm$^{-1}$ to 5000 cm$^{-1}$ and further alternatively from 4500 cm$^{-1}$ to 4750 cm$^{-1}$ within a first margin for error.

8. The method according to claim 1, characterized in that the NIR measurement spectrum is compared with a plurality of NIR reference spectrums from a spectral reference library.

9. The method according to claim 1, characterized in that the finished medicinal product to be determined is in a closed disposable primary packaging.

10. The method according to claim 1, characterized in that the finished medicinal product to be determined is in a container of the closed disposable primary packaging, which container is made of glass and/or plastics material.

11. The method according to claim 1, characterized in that, when the NIR measurement spectrum is measured, at least one optical measuring method from the following group of optical measuring methods is used: absorption measurement, reflection measurement and transmission measurement.

12. A device for determining a finished medicinal product, comprising:
a test sample receptacle adapted to receive, as a test sample, a finished medicinal product to be determined in a closed primary packaging;
a measuring device adapted to capture an NIR measurement spectrum for the finished medicinal product to be determined through the closed primary packaging; and
an evaluation unit adapted
to compare the NIR (near infrared) measurement spectrum with an NIR (near infrared) reference spectrum which is assigned to a medicinal product or a medicinal product active ingredient, wherein the NIR reference spectrum is assigned to a medicinal product active ingredient formed as a biosimilar; and
to determine that the finished medicinal product to be determined contains the medicinal product or the medicinal product active ingredient when the NIR measurement spectrum and the NIR reference spectrum correspond within a margin for error.

* * * * *